US008003227B2

(12) United States Patent
Vestweber et al.

(10) Patent No.: US 8,003,227 B2
(45) Date of Patent: Aug. 23, 2011

(54) ORGANIC ELECTROLUMINESCENT ELEMENT

(75) Inventors: Horst Vestweber, Gilserberg (DE); Anja Gerhard, Veitschöchheim (DE); Philipp Stössel, Frankfurt (DE)

(73) Assignee: Merck Patent GmbH, Darmstadt (DE)

(*) Notice: Subject to any disclaimer, the term of this patent is extended or adjusted under 35 U.S.C. 154(b) by 1120 days.

(21) Appl. No.: 10/580,491

(22) PCT Filed: Nov. 24, 2004

(86) PCT No.: PCT/EP2004/013314
§ 371 (c)(1),
(2), (4) Date: May 23, 2006

(87) PCT Pub. No.: WO2005/053055
PCT Pub. Date: Jun. 9, 2005

(65) Prior Publication Data
US 2007/0051944 A1 Mar. 8, 2007

(30) Foreign Application Priority Data
Nov. 27, 2003 (DE) .................. 103 56 099

(51) Int. Cl.
*H01L 51/00* (2006.01)
(52) U.S. Cl. .................. 428/690; 257/40; 313/504
(58) Field of Classification Search .......... 428/690; 257/40; 313/504
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,438,138 A | 8/1995 | Henneberger et al. | |
| 5,621,131 A | 4/1997 | Kreuder et al. | |
| 5,716,722 A | 2/1998 | Hamada et al. | |
| 5,840,217 A * | 11/1998 | Lupo et al. ............... | 252/583 |
| 6,225,467 B1 | 5/2001 | Esteghamatian et al. | |
| 6,229,012 B1* | 5/2001 | Hu et al. ................ | 544/180 |
| 6,352,791 B1 | 3/2002 | Fink et al. | |
| 6,653,438 B1 | 11/2003 | Spreitzer et al. | |
| 2002/0034656 A1 | 3/2002 | Thompson et al. | |
| 2002/0034659 A1 | 3/2002 | Nishi et al. | |
| 2003/0022019 A1 | 1/2003 | Seo et al. | |
| 2003/0039858 A1* | 2/2003 | Igarashi et al. ........... | 428/690 |
| 2003/0168970 A1* | 9/2003 | Tominaga et al. ......... | 313/504 |
| 2003/0198831 A1* | 10/2003 | Oshiyama et al. ......... | 428/690 |
| 2004/0135131 A1 | 7/2004 | Treacher et al. | |
| 2004/0147742 A1* | 7/2004 | Wong et al. ............... | 544/230 |
| 2005/0234240 A1 | 10/2005 | Stossel et al. | |
| 2006/0208222 A1 | 9/2006 | Ise | |

FOREIGN PATENT DOCUMENTS

| | | |
|---|---|---|
| DE | 44 46 818 | 7/1996 |
| DE | 103 30 761 | 2/2005 |
| DE | 103 37 346 | 3/2005 |
| EP | 0 676 461 | 10/1995 |
| EP | 0 842 208 | 5/1998 |
| EP | 0 894 107 | 12/1999 |
| EP | 1 191 612 | 3/2002 |
| EP | 1 191 613 | 3/2002 |
| EP | 1 191 614 | 3/2002 |
| EP | 1 202 358 | 5/2002 |
| EP | 1 385 221 | 1/2004 |
| JP | 2002-212170 | 7/2002 |
| JP | 2003-045662 A | 2/2003 |
| JP | 2003-086381 | 3/2003 |
| JP | 2003-282270 | 10/2003 |
| JP | 2004-103576 A | 4/2004 |
| JP | 2004-339070 A | 12/2004 |
| WO | WO-98/01011 | 1/1998 |
| WO | WO-99/40051 | 8/1999 |
| WO | WO-00/22026 | 4/2000 |
| WO | WO-00/57676 | 9/2000 |
| WO | WO 00/70655 | 11/2000 |
| WO | WO-01/41512 | 6/2001 |
| WO | WO-02/02714 | 1/2002 |
| WO | WO-02/15645 | 2/2002 |
| WO | WO-02/074015 | 9/2002 |
| WO | WO-02/077060 | 10/2002 |
| WO | WO-03/040257 | 5/2003 |
| WO | WO-03/084972 | 10/2003 |
| WO | WO-2004/026886 | 4/2004 |
| WO | WO-2004/041901 | 5/2004 |
| WO | WO-2004/077885 | 9/2004 |
| WO | WO-2004/081017 | 9/2004 |
| WO | WO-2004/093207 | 10/2004 |
| WO | WO-2004/113412 | 12/2004 |

OTHER PUBLICATIONS

Wu cc et. al. "Highly bright blue organic light emitting device using spirobifluorene compounds" Applied Physics vol. 81, No. 4, p. 577-579.*
Wuest et. al., Molecular Tectonics . . . 9,9' Spirobifluoene, 2004, J. Org. Chem., vol. 69, pp. 1762-1775.*
C.C. Wu et al., "Highly bright blue organic light-emitting devices using spirobifluorene-cored conjugated compounds," *Applied Physics Letters*, vol. 81, No. 4, pp. 577-579 (Jul. 22, 2002).
J. Fournier et al., "Molecular Tectonics, Porous Hydrogen-Bonded Networks Built from Derivatives of 9,9'-Spirobifluorene," *J. Org. Chem.*., vol. 69, pp. 1762-1775 (2004).
English Translation of JP 2003-045662.
English Translation of JP 2004-339070.

* cited by examiner

*Primary Examiner* — D. Lawrence Tarazano
*Assistant Examiner* — Gregory Clark
(74) *Attorney, Agent, or Firm* — Connolly Bove Lodge & Hutz LLP

(57) ABSTRACT

The present invention relates to the improvement of phosphorescent organic electroluminescent devices by using materials of the formula (1), preferably triazines, pyrimidines, pyridazines and pyrazines, in the hole-blocking layer.

25 Claims, No Drawings

ORGANIC ELECTROLUMINESCENT ELEMENT

RELATED APPLICATIONS

This application is a national stage application (under 35 U.S.C. 371) of PCT/EP2004/013314 filed Nov. 24, 2004 which claims benefit to German application 103 56 099.8 filed Nov. 27, 2003.

Organic and organometallic compounds are used as functional materials in a number of different applications, which can be ascribed to the electronics industry in the broadest sense. The organic electroluminescent devices based on organic components (general description of the structure cf. U.S. Pat. No. 4,539,507 and U.S. Pat. No. 5,151,629) and the individual components thereof, organic light-emitting diodes (OLEDs), have already been introduced onto the market, as confirmed by the automobile radios with an "organic display" from Pioneer or a digital camera from Kodak. Further products of this type are just about to be introduced. Nevertheless, significant improvements are still necessary here in order to make these displays a true competitor to the liquid-crystal displays (LCDs) which currently dominate the market, or to surpass the latter.

A development which has emerged in recent years is the use of organometallic complexes which exhibit phosphorescence instead of fluorescence (M. A. Baldo et al., *Appl. Phys. Lett.* 1999, 75, 4-6). For theoretical spin-statistical reasons, an up to four-fold increase in energy and power efficiency is possible using organometallic compounds as phosphorescence emitters. Whether this new development will succeed depends on whether it is possible to find corresponding device compositions which are also able to implement these advantages (triplet emission=phosphorescence compared with singlet emission=fluorescence) in OLEDs. It is not only the development of the organometallic compounds themselves that is of importance here, but also, in particular, the development of further materials specifically required for this purpose, such as, for example, matrix or hole-blocking materials.

An organic electroluminescent device usually consists of a plurality of layers applied one on top of the other by means of vacuum methods or various printing techniques. For phosphorescent organic electroluminescent devices, these layers are in detail:

1. outer plate=substrate (usually glass or plastic sheet);
2. transparent anode (usually indium-tin oxide, ITO);
3. hole-injection layer (HIL): for example based on copper phthalocyanine (CuPc) or conductive polymers;
4. hole-transport layer(s) (HTL): usually based on triarylamine derivatives, for example 4,4',4"-tris(N-1-naphthyl-N-phenylamino)triphenylamine (NaphDATA) as the first layer and N,N'-di-(1-naphthyl)-N,N'-diphenylbenzidine (NPB) as the second layer;
5. emission layer(s) (EML): usually comprising a matrix material in phosphorescent devices, for example 4,4'-bis(carbazol-9-yl)biphenyl (CBP) which is doped with a phosphorescent dye, for example tris(phenylpyridyl)iridium ($Ir(PPy)_3$) or tris-(2-benzothiophenylpyridyl)iridium ($Ir(BTP)_3$);
6. hole-blocking layer (HBL): usually comprising BCP (2,9-dimethyl-4,7-diphenyl-1,10-phenanthroline=bathocuproin) or bis(2-methyl-8-hydroxyquinolato)-(4-phenylphenolato)aluminium(III) (BAlq);
7. electron-transport layer (ETL): usually based on aluminium tris-8-hydroxyquinolinate ($AlQ_3$);
8. electron-injection layer (EIL, also known as insulator layer=ISL): thin layer of a material having a high dielectric constant, such as, for example, LiF, $Li_2O$, $BaF_2$, MgO, NaF;
9. cathode: generally metals, metal combinations or metal alloys having a low work function, for example Ca, Ba, Cs, Mg, Al, In, Mg/Ag.

Depending on the device structure, a plurality of these layers may also coincide or each of these layers does not necessarily have to be present.

However, there are still considerable problems requiring urgent improvement in order to facilitate high-quality full-colour applications:

1. For example, the operating lifetime of OLEDs, in particular, is still too short, meaning that it has hitherto only been possible to implement simple applications commercially.
2. The short lifetime gives rise to a secondary problem: especially for full-colour applications ("full-colour displays"), it is particularly poor if the individual colours age at different rates, as is currently the case. This results in that the white point shifts significantly before the end of the lifetime (which is generally defined by a drop to 50% of the initial brightness), i.e. the colour fidelity of the representation in the display worsens. In order to circumvent this, some display manufacturers define the lifetime as 70% or 90% lifetime (i.e. drop of the initial brightness to 70% or 90% of the initial value). However, this results in the lifetime becoming even shorter.
3. The ageing processes are generally accompanied by an increase in the voltage. This effect makes voltage-driven organic electroluminescent devices difficult or impossible. However, current-driven addressing is more complex and expensive in this case.
4. Precisely in the case of efficient phosphorescent OLEDs, the requisite operating voltage is quite high and therefore has to be reduced in order to improve the power efficiency.
5. Although the efficiency, in particular the power efficiency (measured in lm/W), of phosphorescent OLEDs is acceptable, improvements are still also desired here.
6. The structure of the OLEDs is complex and technologically complicated due to the large number of organic layers; a reduction in the number of layers is desirable for production in order to reduce the number of production steps, thus simplifying the technology and increasing production reliability.

The above-mentioned reasons make improvements necessary in the production of OLEDs.

In the case of phosphorescent OLEDs, a hole-blocking layer (HBL) is usually used after the emitter layer in order to increase the efficiency and lifetime. These device structures are usually optimised according to the criterion of maximum efficiency. BCP (bathocuproin) is frequently used as hole-blocking material (HBM), enabling very good efficiencies to be achieved (D. F. O'Brien et al., *Appl. Phys. Lett.* 1999, 74, 442), but with the crucial disadvantage that the lifetime of the OLEDs comprising BCP is greatly restricted. T. Tsutsui et al. (Japanese *J. Appl. Phys.* 1999, 38, LI 502) indicate the low stability of BCP as the reason for the poor lifetime, meaning that these devices cannot be used in high-quality displays. A further hole-blocking material is bis(2-methyl-8-hydroxyquinolato)(4-phenylphenolato)aluminium(III) (BAlq). This has enabled the stability and lifetime of the devices to be significantly improved, but with the side effect that the quantum efficiency of the devices comprising BAlq is about 40% lower than with BCP (T. Watanabe et al., *Proc. SPIE* 2001, 4105, 175). Kwong et al. (*Appl. Phys. Lett.* 2002, 81, 162) thus achieved lifetimes of 10,000 h at 100 $cd/m^2$ using tris (phenylpyridyl)iridium(III). However, this device exhibited an efficiency of only 19 cd/A, which is well behind the state of the art. Thus, although good lifetimes are possible using BAlq, overall it is, however, not a satisfactory hole-blocking material since the efficiency achieved is too low.

It is clearly evident from this description that the hole-blocking materials (HBMs) used to date, such as, for example, BCP or BAlq, result in unsatisfactory side effects. Thus, there continues to be a demand for hole-blocking materials which result in good efficiencies in OLEDs, but at the same time also result in long life-times. Surprisingly, it has now been found that OLEDs which comprise certain heterocycles—listed below—in particular diazines and triazines, as hole-blocking materials have significant improvements over the prior art. Using these hole-blocking materials, it is possible simultaneously to obtain high efficiencies and good lifetimes, which is not possible using materials in accordance with the prior art. In addition, it has been found that a separate electron-transport layer does not necessarily have to be used with the novel hole-blocking materials, which represents a technological advantage, and that in addition the operating voltages can consequently be significantly reduced, which corresponds to higher power efficiency.

The use of triazines, pyrimidines, pyrazines and pyridazines as emission or charge-transport material in organic electroluminescent devices has already been described in the literature. These materials have been described as fluorescent emitters or in combination with fluorescent emitters. U.S. Pat. No. 6,352,791 and U.S. Pat. No. 6,225,467 describe triazines, in particular specifically substituted triazines, as electron-transport materials in OLEDs. A. Bacher et al. (*Inorg. and Org. Electroluminescence* (*Int. Workshop on Electroluminescence*) 1996, 109-112) report a three-fold higher efficiency if triazine derivatives are incorporated as electron-transport layer between AlQ$_3$ as emitter and the cathode. No mention is made of the lifetime. Pyrazines as electron-transport materials are described, for example, by T. Oyamada et al. (*Chem. Lett.* 2003, 32, 388). On the other hand, substituted pyrimidine and triazine derivatives can also be employed as hole-transport materials in OLEDs (U.S. Pat. No. 5,716,722). JP 2002/212170 describes triazine derivatives as electrofluorescent compounds, as do J. Pang et al. (*J. Mater. Chem.* 2002, 12, 206).

JP 2003/282270 describes phenylpyridine derivatives in OLEDs. In addition to numerous other groups, these may also contain triazine, pyrimidine, pyrazine or pyridazine. However, the positive effect of these compounds is attributed to the phenylpyridne units and not to the triazine, pyrimidine, pyrazine or pyridazine, and consequently this application should be regarded as a chance disclosure.

It cannot be seen from the prior art cited above how diazine and triazine derivatives could usefully be used in phosphorescent OLEDs since these materials are described both as electron conductors and also as hole conductors or as (fluorescent) emitters. In particular, it is described in the literature by leading experts in the field of phosphorescent OLEDs (R. C. Kwong, M. E. Thompson, S. R. Forrest et al., *Appl. Phys. Lett.* 2002, 81, 162) that electron-deficient heterocycles, such as, for example, triazines, as hole-blocking materials in phosphorescent OLEDs result in very poor lifetimes, typically in the region of less than 100 h at brightnesses of 500 cd/m$^2$, which is well behind the state of the art. A person skilled in the art would have been able to derive from this that this combination is thus unsuitable for achieving a technical improvement. This in no way suggests that good results can be achieved therewith.

The invention relates to an organic electroluminescent device comprising an anode, a cathode and an emission layer, consisting of at least one matrix material which is doped with at least one phosphorescent emitter, characterised in that a hole-blocking layer which comprises a compound of the formula (1)

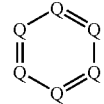

(Formula 1)

where the following applies to the symbols and indices used:

Q is on each occurrence, identically or differently, N or CR, with the proviso that at least two and a maximum of four Q stand for nitrogen;

R is on each occurrence, identically or differently, H, NO$_2$, CN, N(R$^1$)$_2$, a straight-chain, branched or cyclic alkyl or alkoxy group having 1 to 40 C atoms, in which one or more non-adjacent CH$_2$ groups may be replaced by —R$^1$C=CR$^1$—, —C≡C—, Si(R$^1$)$_2$, Ge(R$^1$)$_2$, Sn(R$^1$)$_2$, —O—, —S— or —NR$^1$— and in which one or more H atoms may be replaced by F or an aromatic group R$^1$, or an aromatic or heteroaromatic ring system or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system, or an aromatic or heteroaromatic ring system bonded via a divalent group —Z— or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system;

R$^1$ is on each occurrence, identically or differently, H or an aliphatic, aromatic or heteroaromatic hydrocarbon radical having 1 to 20 C atoms, in which a plurality of substituents R$^1$ or R$^1$ with R may also define a further mono- or polycyclic, aliphatic or aromatic ring system;

Z is on each occurrence, identically or differently, a straight-chain, branched or cyclic, preferably conjugated radical having 1 to 40 C atoms, which is preferably in conjugation with the two other substituents, where the number of atoms in Z which link the group of the formula (1) and the aromatic radical is preferably an even number, where one or more non-adjacent C atoms may be replaced by —O—, —S— or —NR$^1$— or one or more C atoms may be substituted by a radical R$^1$ or halogen;

with the proviso that R does not contain substituted or unsubstituted phenylpyridine, is incorporated between the emission layer and the cathode.

The compound of the formula (1) preferably has a molecular weight of at least 350 g/mol.

For the purposes of this invention, an aromatic or heteroaromatic ring system is taken to mean a system which does not necessarily comprise only aryl groups or heteroaryl groups, but instead in which a plurality of aryl or heteroaryl groups may also be interrupted by a short non-aromatic unit, such as, for example, sp$^3$-hybridised C, O, N, etc. Thus, for example, systems such as 9,9'-spirobifluorene, 9,9-diarylfluorene, triarylamine, diaryl ether, etc., should also be understood as aromatic systems.

The OLED may also comprise further layers, such as, for example, hole-injection layer, hole-transport layer, electron-injection layer and/or electron-transport layer. However, it should be pointed out that all these layers do not necessarily have to be present. Thus, it has been found that OLEDs according to the invention which comprise compounds of the formula (1) in the hole-blocking layer continue to give comparably good efficiencies and lifetimes with reduced operating voltage if separate electron-injection and electron-transport layers are not used. The hole-blocking layer according to the invention preferably comprises at least 50% of compounds of the formula (1), particularly preferably at least 80%, very particularly preferably consists only of compounds of the formula (1).

Preferred structures of the formula (1) contain two or three nitrogen atoms in the ring. These are diazines or triazines, i.e. pyridazines (1,2-diazines), pyrimidines (1,3-diazines), pyrazines (1,4-diazines), 1,2,3-, 1,2,4- or 1,3,5-triazines. Particular preference is given to pyrimidines or triazines, in particular 1,2,4- and 1,3,5-triazines.

Although evident from the description, it should be expressly pointed out here that the hole-blocking material may also comprise more than one such diazine or triazine unit.

Compounds which have proven to be particularly suitable hole-blocking materials are those which have a non-planar structure. While the skeleton (i.e. the six-membered ring of the diazine or triazine) always has a planar structure, corresponding substituents (present in R) may cause a deviation from planarity of the structure as a whole. This is the case, in particular, if at least one of the substituents R contains an $sp^3$-hybridised carbon atom (or correspondingly also silicon, germanium, nitrogen, etc.), which consequently has approximately tetrahedral (or in the case of nitrogen pyramidal) geometry.

Preferred hole-blocking materials are therefore compounds of the formula (1) in which at least one substituent R contains at least one $sp^3$-hybridised carbon atom.

In order to achieve a more significant deviation from planarity, it is preferred for this $sp^3$-hybridised carbon atom to be a secondary, tertiary or quaternary carbon atom, particularly preferably a tertiary or quaternary carbon atom, very particularly preferably a quaternary carbon atom. A secondary, tertiary or quaternary carbon atom is taken to mean a carbon atom having two, three or four substituents other than hydrogen.

Particular preference is given to compounds of the formula (1) which contain a 9,9'-spirobifluorene derivative, a 9,9-disubstituted fluorene derivative, a 6,6- and/or 12,12-di- or tetrasubstituted indenofluorene derivative, a triptycene derivative (preferably linked via position 9 and/or 10) or a tetraarylmethane derivative in at least one of the radicals R. The diazine or triazine or tetrazine unit here may also be bonded, for example, in the 9-position of the fluorene or in the 6- and/or 12-position of the indenofluorene.

Very particular preference is given to compounds of the formula (1) which contain a 9,9'-spirobifluorene derivative in at least one of the radicals R.

The glass transition temperature of the compounds of the formula (1) is preferably >100° C., particularly preferably >120° C., very particularly preferably >140° C. It has been found that the glass transition temperature of compounds in which at least one of the radicals R contains a spirobifluorene derivative is usually in this range. This justifies the preference for these materials.

It has been found that the best results (in relation to the efficiency and lifetime) are achieved if the layer thickness of the hole-blocking layer is 1 to 50 nm, preferably 5 to 30 nm.

It has furthermore been found that particularly good results, in particular in relation to the operating voltage and power efficiency, are achieved if a separate electron-transport layer is not incorporated between the hole-blocking layer and the cathode or the electron-injection layer. Preference is thus given to an electroluminescent device according to the invention which does not comprise an electron-transport layer and in which the hole-blocking layer is directly adjacent to the electron-injection layer or the cathode. This is a surprising result since the same device structure with BCP as hole-blocking material without an ETL gives significantly shorter lifetimes.

The present invention is explained in greater detail by the following examples of hole-blocking materials of the formula (1), without wishing to be restricted thereto. Possible substituents on the spirobifluorene unit or the corresponding other units and also possible further substituents on the triazine are not shown for reasons of clarity. The person skilled in the art will be able to produce further electroluminescent devices according to the invention comprising similar hole-blocking materials from the description and the examples given without an inventive step.

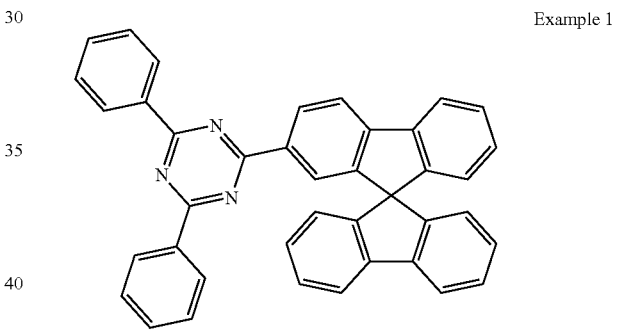

Example 1

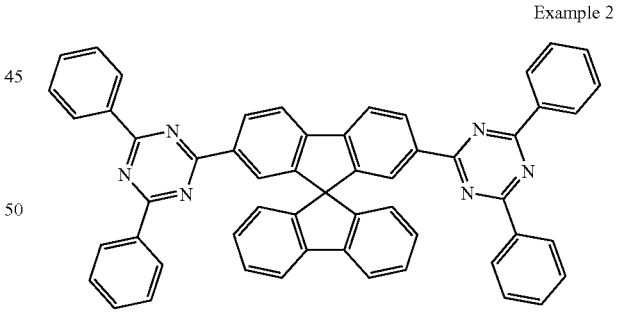

Example 2

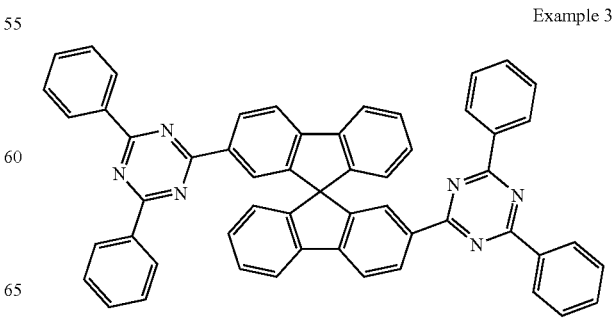

Example 3

Example 4
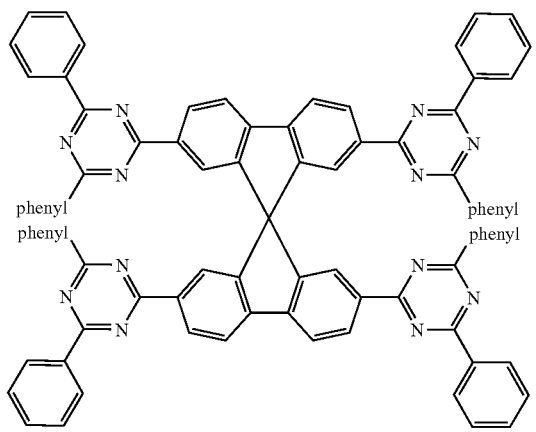
Example 5
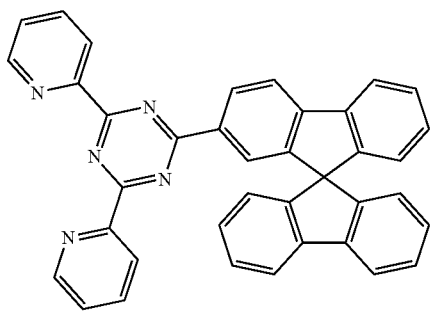
Example 6
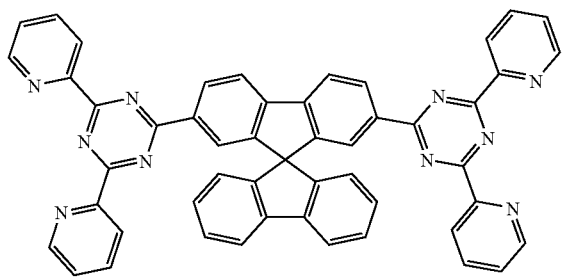
Example 7
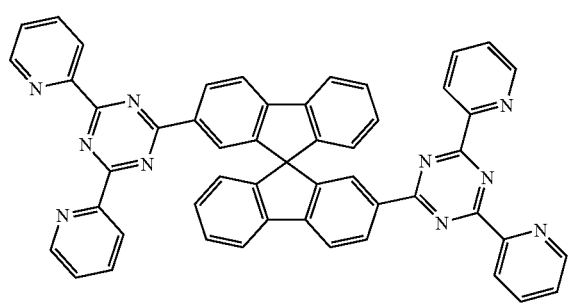
Example 8
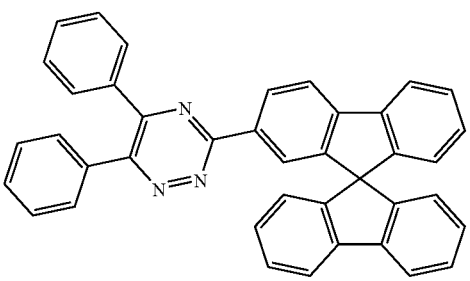
Example 9
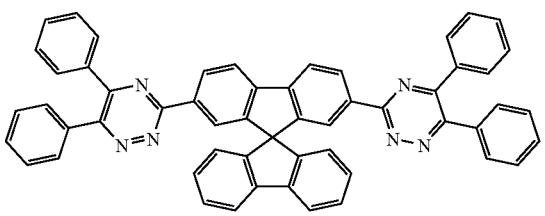
Example 10
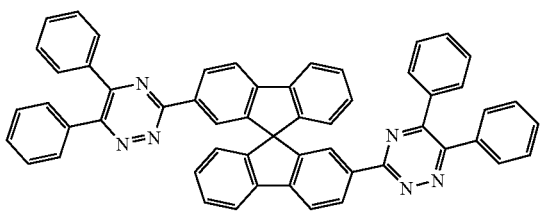
Example 11
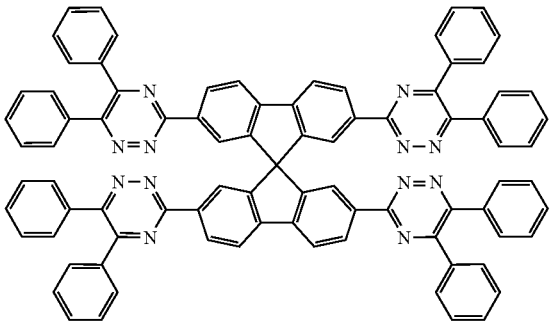
Example 12
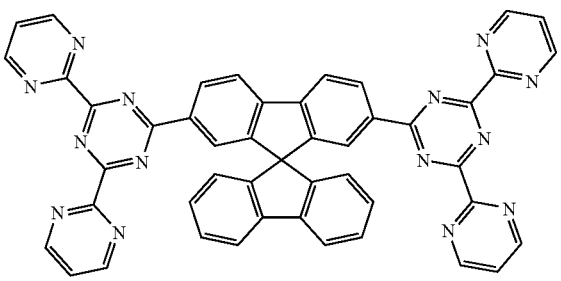
Example 13
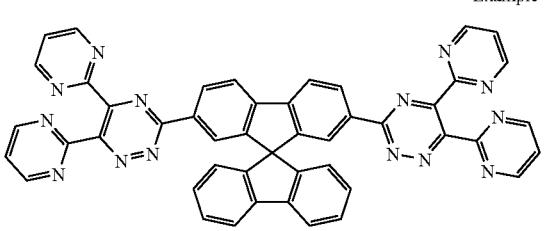

Example 14
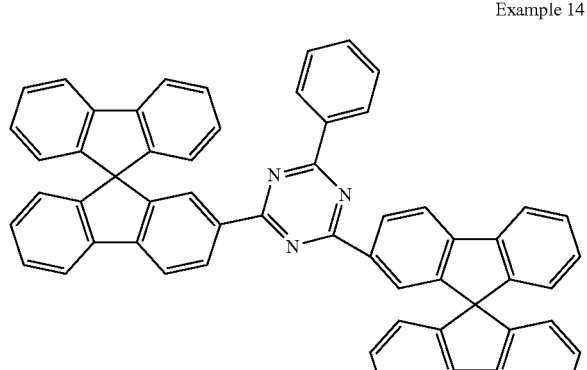
Example 15
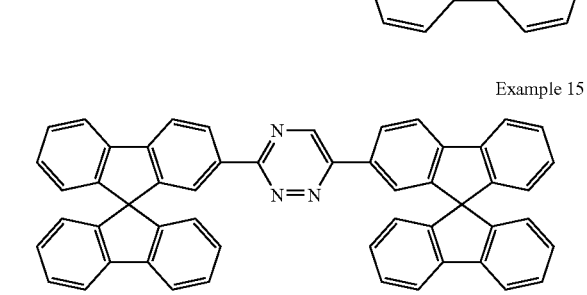
Example 16
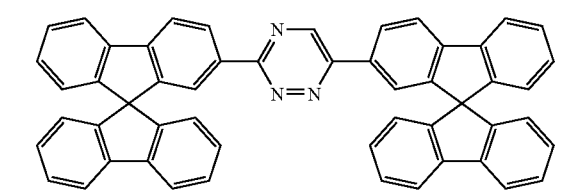
Example 17
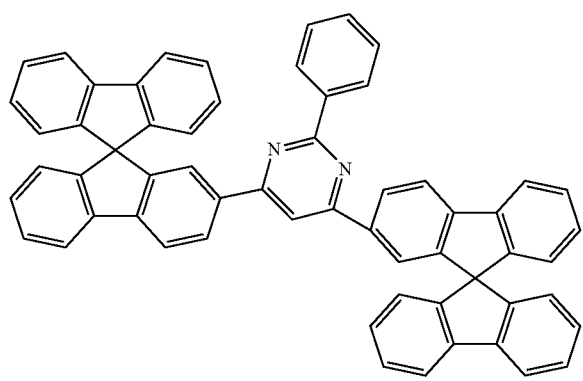
Example 18
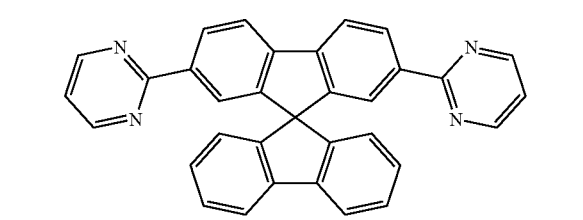
Example 19
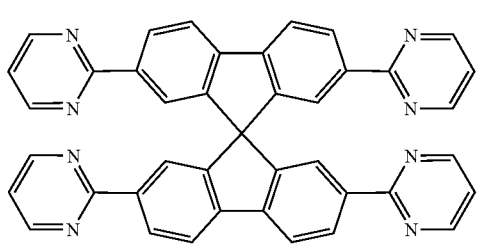
Example 20
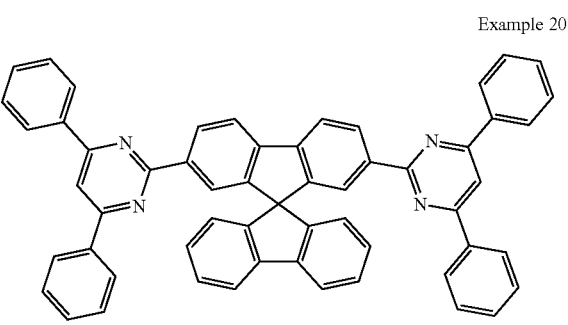
Example 21
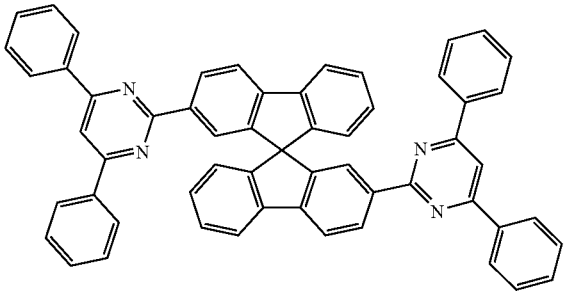
Example 22
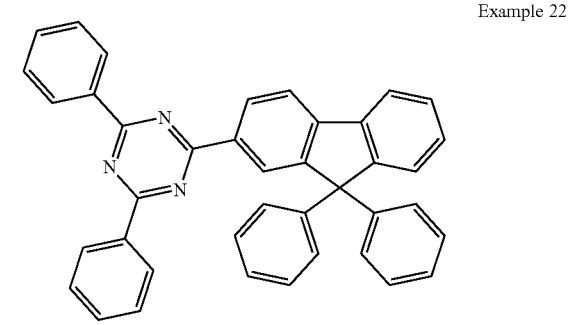
Example 23
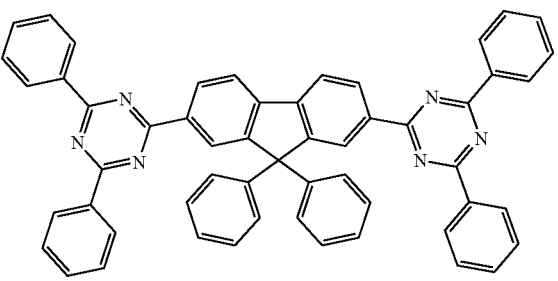

Example 24
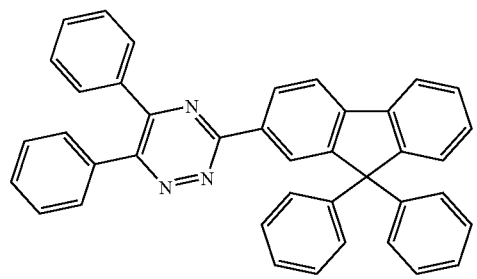
Example 25
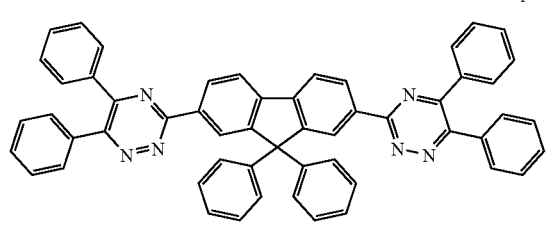
Example 26
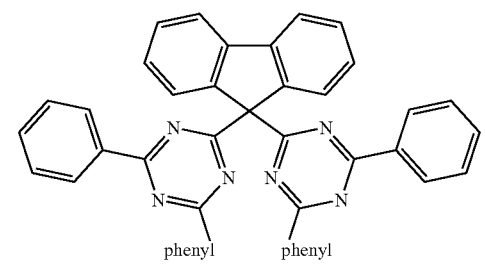
Example 27
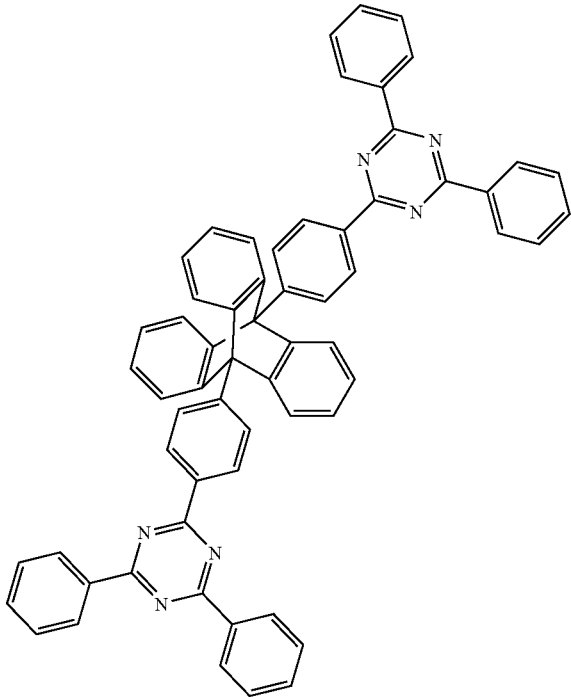
Example 28
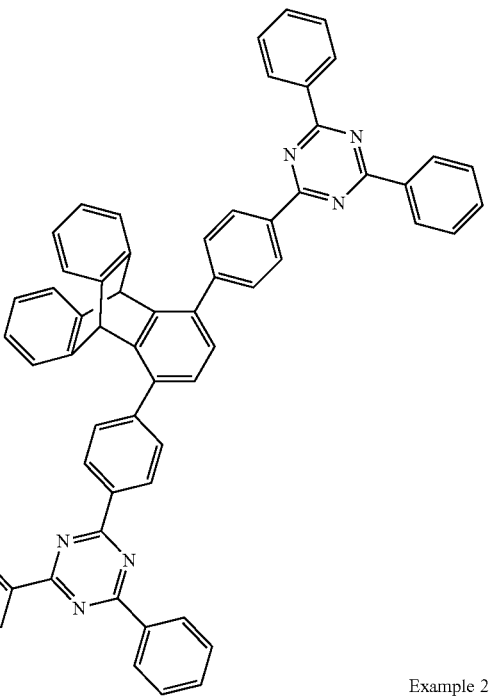
Example 29
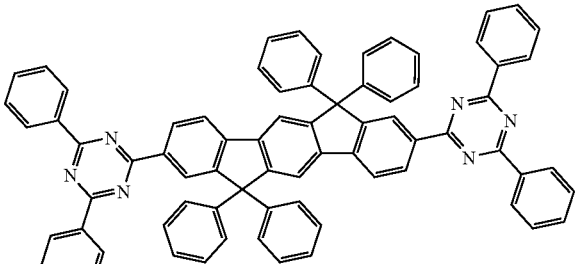
Example 30
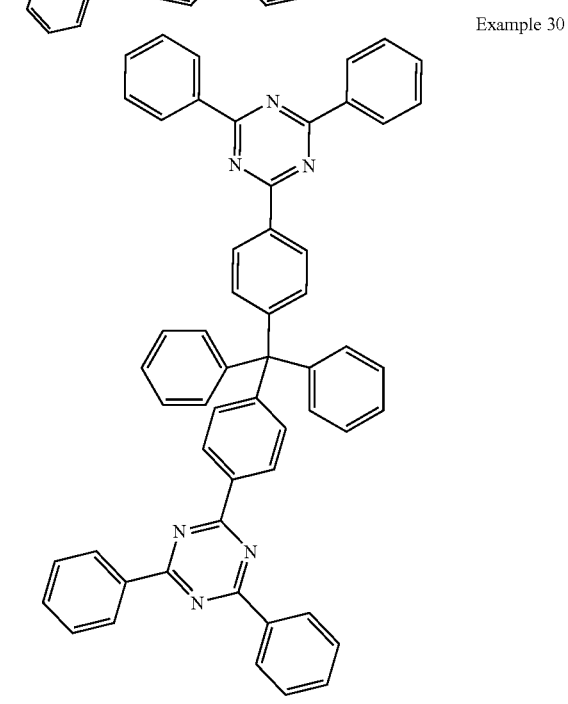

Example 31

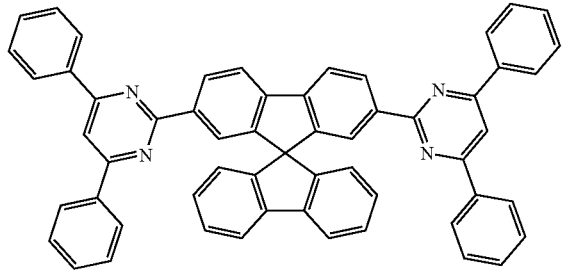

Example 32

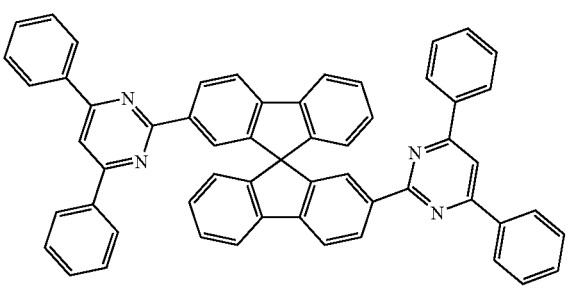

The matrix for the phosphorescent emitter is preferably selected from the classes of carbazoles, for example in accordance with WO 00/057676, EP 1202358 and WO 02/074015, ketones and imines, for example in accordance with WO 04/093207, phosphine oxides, phosphine sulfides, phosphine selenides, phosphazenes, sulfones, sulfoxides, for example in accordance with DE 10330761.3, the silanes, the polypodal metal complexes, for example in accordance with WO 04/081017, or oligophenylenes based on spirobifluorenes, for example in accordance with EP 676461 and WO 99/40051; particular preference is given to ketones, phosphine oxides, sulfoxides and oligophenylenes based on spirobifluorenes.

The phosphorescent emitter is preferably a compound which contains at least one element having an atomic number of greater than 36 and less than 84. The phosphorescent emitter particularly preferably contains at least one element having an atomic number of greater than 56 and less than 80, very particularly preferably molybdenum, tungsten, rhenium, ruthenium, osmium, rhodium, iridium, palladium, platinum, silver, gold or europium, for example in accordance with WO 98/01011, US 02/0034656, US 03/0022019, WO 00/70655, WO 01/41512, WO 02/02714, WO 02/15645, EP 1191613, EP 1191612, EP 1191614, WO 03/040257, WO 03/084972 and WO 04/026886.

One or more layers in the organic electroluminescent device are preferably coated by a sublimation process, in which the low-molecular-weight materials are vapour-deposited in vacuum sublimation units at a pressure below $10^{-5}$ mbar, preferably below 10-6 mbar, particularly preferably below $10^{-7}$ mbar.

One or more layers in the organic electroluminescent device are likewise preferably coated by the OVPD (organic vapour phase deposition) process or with the aid of carrier-gas sublimation, in which the low-molecular-weight materials are applied at a pressure between $10^{-5}$ mbar and 1 bar.

One or more layers in the organic electroluminescent device are likewise preferably coated by a printing process, such as, for example, flexographic printing or offset printing, but particularly preferably LITI (light induced thermal imaging, thermal transfer printing) or ink-jet printing.

The emitting devices described above have the following surprising advantages over the prior art:
1. The efficiency of corresponding devices is higher compared with systems in accordance with the prior art which comprise BAlq as HBL.
2. The lifetime of corresponding devices is longer compared with systems comprising BCP as HBL. Devices are thereby obtained whose lifetime and efficiency are comparable with the best values in accordance with the prior art and in which not only one of the two properties gives good results, as is the case with BAlq or BCP.
3. The operating voltages are lower in devices according to the invention than in devices in accordance with the prior art.
4. The layer structure can be simplified since there is no need to use a separate electron-transport layer. This is a surprising result since the same device structure with BCP instead of triazine without an electron-transport layer gives significantly worse lifetimes and efficiencies.
5. If an electron-transport layer is not used, a further advantage arises: the operating voltages here are significantly lower; the power efficiency consequently increases considerably. This is a surprising result since the same device structure with BAlq instead of triazine results in an operating voltage which is hardly reduced at all.
6. The production complexity is likewise less without use of an electron-transport layer. This is a considerable technological advantage in the production process since a separate segment of the vapour-deposition unit is required for each organic layer in the conventional production process.

Details on the statements made here are given in the examples described below.

The present application text and the following examples are directed to organic light-emitting diodes and the corresponding displays. In spite of this restriction of the description, it is possible for the person skilled in the art, without further inventive step, also to use the corresponding design according to the invention for other, related devices, for example for organic solar cells (O—SCs), organic transistors, organic integrated circuits or also organic laser diodes (O-lasers), to mention but a few further applications. The present application therefore also relates to these.

Spirobifluorenes which are substituted by triazines are novel and are thus likewise a subject-matter of the present invention.

The invention thus furthermore relates to compounds of the formula (2) comprising at least one spirobifluorene unit, characterised in that at least one triazine unit is bonded to the spirobifluorene Formula (2)

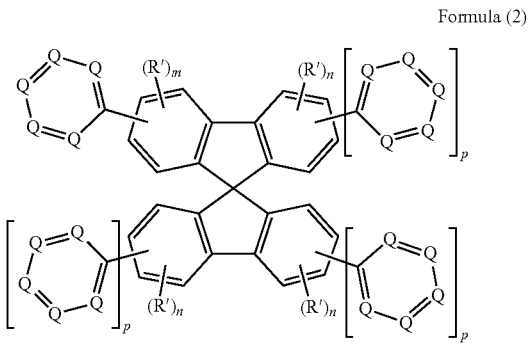

where R and R$^1$ have the same meaning as defined above under formula (1), and the further symbols and indices have the following meaning:

Q is on each occurrence, identically or differently, N or CR, with the proviso that three Q stand for nitrogen and two Q stand for CR;

R' is on each occurrence, identically or differently, R or F, Cl, Br, I, B(R$^1$)$_2$ or B(OR$^1$)$_2$;

m is on each occurrence, identically or differently, 0, 1, 2 or 3;

n is on each occurrence, identically or differently, 0, 1, 2, 3 or 4, with the proviso that n must not be 4 if p=1;

p is on each occurrence, identically or differently, 0 or 1.

The triazine unit can in accordance with the invention be 1,2,3-, 1,2,4- or 1,3,5-triazine. Various triazine derivatives may also be present in a single compound. All the triazines present in a single compound are preferably the same triazine derivative. Particular preference is given to 1,3,5-triazine or 1,2,4-triazine.

The triazine unit is preferably linked to the spirobifluorene in position 2 (or 2', 7 or 7'), i.e. in the para-position to the phenyl-phenyl link of the spirobifluorene.

In preferred structures of the formula (2), the following applies to the symbols and indices:

R is on each occurrence, identically or differently, a straight-chain, branched or cyclic alkyl group having 1 to 10 C atoms, in which one or more non-adjacent CH$_2$ groups may be replaced by —R$^1$C=CR$^1$—, —C≡C—, Si(R$^1$)$_2$, Ge(R$^1$)$_2$, Sn(R$^1$)$_2$, —O—, —S— or —NR$^1$—, or an aromatic or heteroaromatic ring system having 1 to 30 aromatic C atoms, which may be substituted by one or more non-aromatic radicals R, where a plurality of substituents R, both on the same ring and also on different rings, may together in turn define a further mono- or polycyclic, aliphatic or aromatic ring system;

m is on each occurrence, identically or differently, 0 or 1;

n is on each occurrence, identically or differently, 0 or 1;

the further symbols and indices are as defined above under formulae (1) and (2).

In particularly preferred structures of the formula (2), the following applies to the symbols and indices:

R is on each occurrence, identically or differently, an aromatic or heteroaromatic ring system having 1 to 10 aromatic C atoms, which may be substituted by one or more non-aromatic radicals R, as defined above, where a plurality of substituents, R, both on the same ring and also on different rings, may together in turn define a further mono- or polycyclic, aliphatic or aromatic ring system;

R' is on each occurrence, identically or differently, R, a straight-chain, branched or cyclic alkyl group having 1 to 10 C atoms, in which one or more non-adjacent CH$_2$ groups may be replaced by —R$^1$C=CR$^1$—, —C≡C—, Si(R$^1$)$_2$, Ge(R$^1$)$_2$, Sn(R$^1$)$_2$, —O—, —S— or —NR—, or Br, I or B(OR$^1$)$_2$;

m is equal to 0;

n is on each occurrence, identically or differently, 0 or 1;

the further symbols and indices are as defined above under formulae (1) and (2).

Preference is furthermore given to compounds of the formula (2) in which two triazine units are present, both bonded to the same fluorene sub-unit of the spirobifluorene, preferably in positions 2 and 7.

The compounds of the formula (2) according to the invention described above can also be used, for example, as comonomers for the production of corresponding polymers or also as the core of dendrimers. Particularly suitable for this purpose are compounds of the formula (2) which contain corresponding functionalities which are suitable for the subsequent reaction, such as, for example, halogens, in particular bromine or iodine, or boronic acids or corresponding derivatives. Thus, these compounds can be copolymerised, inter alia, into soluble polyfluorenes (for example in accordance with EP 842208 or WO 00/22026), polyspirobifluorenes (for example in accordance with EP 707020 or EP-A-894107), polyindenofluorenes (for example in accordance with WO 04/041901 or EP 03014042.0 which is the priority document of WO 04/113412) or polydihydrophenanthrenes (for example in accordance with DE 10337346.2). These polymers or dendrimers can be used as hole-blocking material in organic electroluminescent devices.

The materials of the formula (2) may furthermore also be functionalised further by the reaction types indicated above, for example, and thus converted into extended hole-blocking materials of the formula (2). An example which may be mentioned here is SUZUKI functionalisation using arylboronic acids or HARTWIG-BUCHWALD functionalisation using amines.

The present invention furthermore relates to the use of compounds of the formula (2) or polymers or dendrimers which comprise these compounds, in electronic devices. The invention likewise relates to electronic devices, such as, for example, organic light-emitting diodes, organic solar cells, organic transistors, organic integrated circuits or organic laser diodes, which comprise at least one compound of the formula (2) or a corresponding polymer or dendrimer.

The OLEDs are produced by a general process which has been adapted in individual cases to the respective circumstances (for example layer-thickness variation in order to optimise the efficiency or colour). The hole-blocking layer used for the production of the devices according to the invention was a compound of the formula (1), and the electron-transport layer is optionally omitted. Electroluminescent devices according to the invention can be produced as described, for example, in DE10330761.3.

EXAMPLES

The following syntheses were carried out, unless indicated otherwise, under a protective-gas atmosphere in dried solvents. The starting materials were purchased from ALDRICH (potassium fluoride (spray-dried), tri-tert-butylphosphine, palladium-(II)acetate). 3-Chloro-5,6-diphenyl-1,2,4-triazine was purchased from SYNCHEM OHG. 2',7'-di-tert-butyl-spiro-9,9'-bifluorene-2,7-bisboronic acid glycol ester was prepared as described in WO 02/077060, and 2-chloro-4,6-diphenyl-1,3,5-triazine was prepared as described in U.S. Pat. No. 5,438,138. Spiro-9,9'-bifluorene-2,7-bis(boronic acid glycol ester) was prepared analogously to WO 02/077060.

Example 1

Synthesis of 2,7-bis(4,6-diphenyl-1,3,5-triazin-2-yl)-2',7'-di-tert-butylspiro-9,9'-bifluorene (TRI1)

28.4 g (50.0 mmol) of glycol 2',7'-di-tert-butylspiro-9,9'-bifluorene-2,7-bisboronate, 29.5 g (110.0 mmol) of 2-chloro-4,6-diphenyl-1,3,5-triazine and 44.6 g (210.0 mmol) of tripotassium phosphate were suspended in 500 ml of toluene, 500 ml of dioxane and 500 ml of water. 913 mg (3.0 mmol) of tri-o-tolylphosphine and then 112 mg (0.5 mmol) of palladium(II) acetate were added to this suspension, and the reaction mixture was refluxed for 16 h. After cooling, the organic phase was separated off, filtered through silica gel, washed three times with 200 ml of water and subsequently evaporated to dryness. The residue was recrystallised from toluene and from dichloromethane/isopropanol and finally sublimed in a high vacuum (p=5×10$^{-5}$ mbar, T=385° C.). The yield was 39.9 g (44.8 mmol), corresponding to 89.5% of theory.

$^1$H-NMR (CDCl$_3$): [ppm]=8.89 (m, 2H), 8.65 (m, 8H), 8.14 (m, 2H), 8.06 (m, 2H), 7.86 (m, 2H), 7.61-7.50 (m, 12H), 7.47 (m, 2H), 6.79 (m, 2H), 1.16 (s, 18H).

Example 2

Synthesis of 2,7-bis(4,6-diphenyl-1,3,5-triazin-2-yl) spiro-9,9'-bifluorene (TRI2)

Procedure analogous to Example 1, with 2', 7'-di-tert-butylspiro-9,9'-bifluorene-2,7-bis(boronic acid glycol ester) being replaced by 22.8 g (50 mmol) of spiro-9,9'-bifluorene-2,7-bis(boronic acid glycol ester). The yield was 32.3 g (41.5 mmol), corresponding to 82.9% of theory.

$^1$H-NMR (CDCl$_3$): [ppm]=8.90 (m, 2H), 8.64 (m, 8H), 8.14 (m, 2H), 8.09 (m, 2H), 8.01 (m, 2H), 7.61-7.49 (m, 12H), 7.45 (m, 2H), 7.15 (m, 2H), 6.86 (m, 2H).

Example 3

Synthesis of 2,7-bis(5,6-diphenyl-1,2,4-triazin-3-yl)-2',7'-di-tert-butylspiro-9,9'-bifluorene (TRI3)

Procedure analogous to Example 1, with the 2-chloro-4,6-diphenyl-1,3,5-triazine being replaced by 3-chloro-5,6-diphenyl-1,2,4-triazine. The yield was 41.0 g (46.0 mmol), corresponding to 92.0% of theory.

$^1$H-NMR (CDCl$_3$): [ppm]=8.74 (m, 2H), 8.12 (m, 4H), 7.75 (m, 2H), 7.59 (m, 4H), 7.53 (m, 4H), 7.45-7.30 (m, 14H), 6.76 (m, 2H), 1.14 (s, 18H).

Example 4

Device Structure

The following examples show the results for various OLEDs, both with hole-blocking materials of the formula (1) and also with BCP and BAlq as comparative materials. The basic structure, the materials and layer thicknesses used (apart from the HBLs) were identical for better comparability. Phosphorescent OLEDs having the following structure were produced by the above-mentioned general process:

| | |
|---|---|
| PEDOT (HIL) | 60 nm (spin-coated from water; purchased as Baytron P from H. C. Starck; poly-(3,4-ethylenedioxy-2, 5-thiophene)) |
| NaphDATA (HTL) | 20 nm (vapour-deposited; purchased from SynTec; 4,4',4''-tris-(N-1-naphthyl-N-phenyl-amino)triphenylamine) |
| S-TAD (HTL) | 20 nm (vapour-deposited; prepared as described in WO 99/12888; 2,2',7,7'-tetrakis(diphenyl-amino)spirobifluorene) |
| (EML) | 30 nm (vapour-deposited); 10% of IrPPy in bis(9, 9'-spirobifluoren-2-yl) ketone as matrix material |
| (HBL) | materials and layer thicknesses see examples in Table 1 |
| AlQ$_3$ (ETL) | not present in all devices (see Table 1); if present: vapour-deposited (purchased from SynTec; tris(8-hydroxyquinolato)aluminium(III)) |
| Ba/Al (cathode) | 3 nm Ba, 150 nm Al on top. |

These still unoptimised OLEDs were characterised by standard methods; for this purpose, the electroluminescence spectra, the efficiency (measured in cd/A), the power efficiency (measured in lm/W) as a function of the brightness and the lifetime were determined. The lifetime is defined as the time after which the initial brightness of the OLED has dropped to half at a constant current density of 10 mA/cm$^2$.

Table 1 shows the results for the OLEDs according to the invention and some comparative examples (with BCP and BAlq) (Examples 5 to 8). The table only shows the hole-blocking layer (composition and layer thickness). The other layers correspond to the above-mentioned structure. In Example 5, TRI1 is used together with an ETL, in Example 6 without an ETL. In Example 7, TRI2 is used together with an ETL, in Example 8 without an ETL.

The abbreviations used above and in Table 1 correspond to the following compounds:

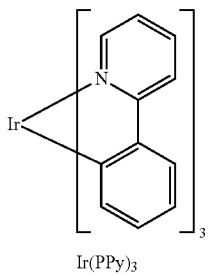

Ir(PPy)$_3$

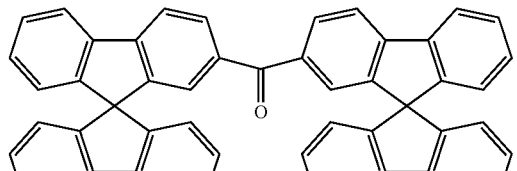

Bis(9,9'-spirobifluoren-2-yl) ketone

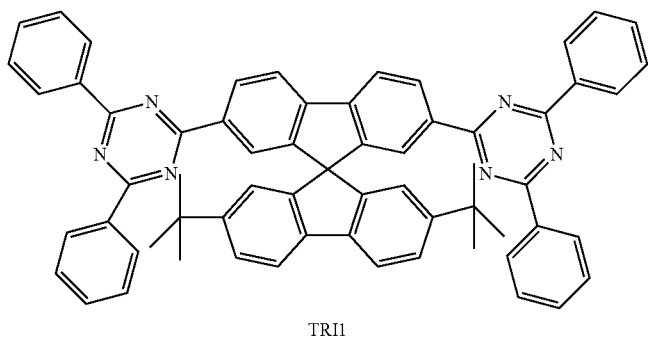

TRI1

-continued

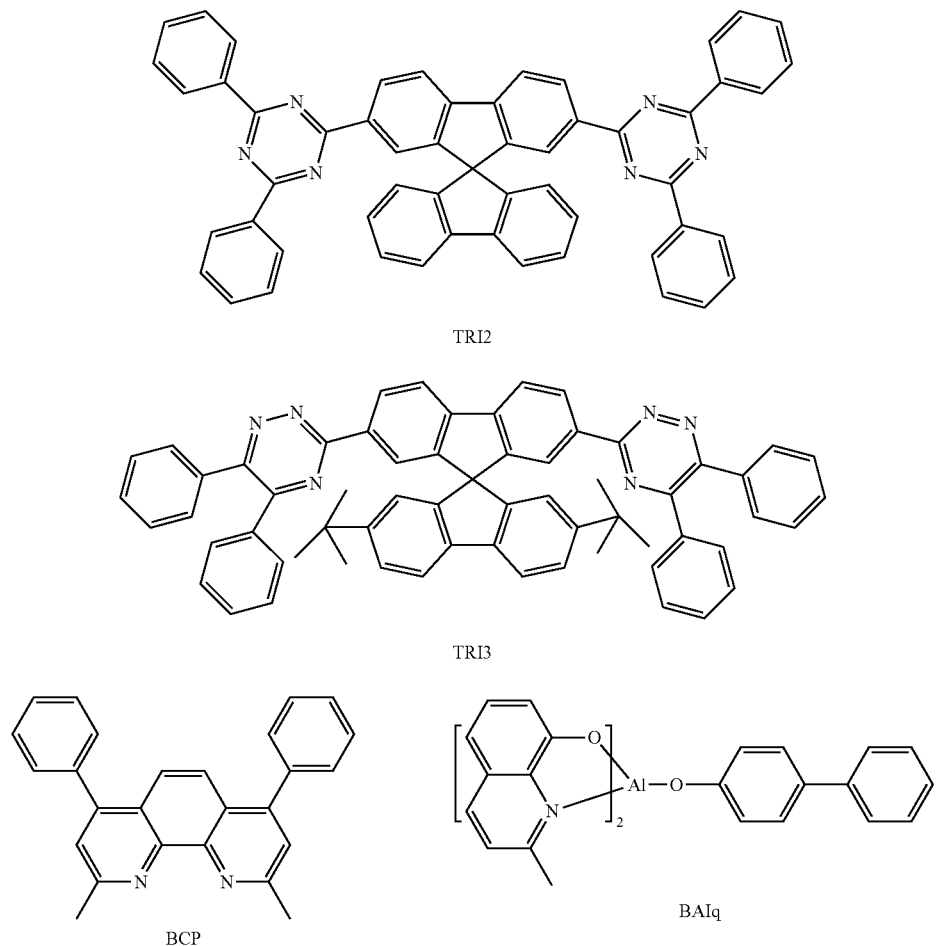

TABLE 1

| Example | HBL | ETL | Max. efficiency (cd/A) | Voltage (V) at 100 cd/m$^2$ | Power eff. (lm/W) at max. efficiency | CIE (x, y) | Lifetime (h) at 10 mA/cm$^2$ |
|---|---|---|---|---|---|---|---|
| Example 5a | TRI1 (10 nm) | AlQ$_3$ (20 nm) | 33.5 | 4.3 | 22.1 | 0.39/0.57 | 780 |
| Example 5b (comparison) | BAlq (10 nm) | AlQ$_3$ (20 nm) | 25.2 | 5.7 | 14.8 | 0.39/0.57 | 510 |
| Example 5c (comparison) | BCP (10 nm) | AlQ$_3$ (20 nm) | 32.6 | 4.8 | 18.2 | 0.39/0.57 | 360 |
| Example 6a | TRI1 (20 nm) | — | 34.2 | 2.7 | 41.4 | 0.38/0.58 | 310 |
| Example 6b (comparison) | BAlq (20 nm) | — | 24.8 | 5.2 | 14.7 | 0.39/0.58 | 240 |
| Example 6c (comparison) | BCP (20 nm) | — | 16.7 | 4.8 | 8.7 | 0.32/0.62 | 80 |
| Example 7a | TRI2 (10 nm) | AlQ$_3$ (20 nm) | 30.9 | 4.0 | 19.2 | 0.39/0.58 | 770 |
| Example 7b (comparison) | cf. Examples 5b and 5c | | | | | | |
| Example 8a | TRI2 (20 nm) | — | 32.9 | 2.9 | 33.8 | 0.38/0.58 | 320 |
| Example 8b (comparison) | cf. Examples 6b and 6c | | | | | | |

In summary, it can be stated that phosphorescent OLEDs which comprise hole-blocking materials of the formula (1) or of the formula (2) have high efficiencies at the same time as long lifetimes and low operating voltages, as can easily be seen from the examples in Table 1. In particular without using an electron-transport layer, very low operating voltages and very high power efficiencies are obtained.

The invention claimed is:

1. Organic electroluminescent device comprising an anode, a cathode and an emission layer, consisting of at least one matrix material which is doped with at least one phosphorescent emitter, characterised in that a hole-blocking layer which comprises a compound of the formula (1)

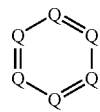 (Formula 1)

where the following applies to the symbols and indices used:
Q is on each occurrence, identically or differently, N or CR, with the proviso that at least two and a maximum of four Q stand for nitrogen;
R is on each occurrence, identically or differently, H, $NO_2$, CN, $N(R^1)_2$, a straight-chain, branched or cyclic alkyl or alkoxy group having 1 to 40 C atoms, in which one or more non-adjacent $CH_2$ groups may be replaced by $-R^1C=CR^1-$, $-C\equiv C-$, $Si(R^1)_2$, $Ge(R^1)_2$, $Sn(R^1)_2$, $-O-$, $-S-$ or $-NR^1-$ and in which one or more H atoms may be replaced by F or an aromatic group $R^1$, or
an aromatic or heteroaromatic ring system or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system, or an aromatic or heteroaromatic ring system bonded via a divalent group $-Z-$ or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system;
$R^1$ is on each occurrence, identically or differently, H or an aliphatic, aromatic or heteroaromatic hydrocarbon radical having 1 to 20 C atoms, in which a plurality of substituents $R^1$ or $R^1$ with R may also define a further mono- or polycyclic, aliphatic or aromatic ring system;
Z is on each occurrence, identically or differently, a straight-chain, branched or cyclic, conjugated radical having 1 to 40 C atoms, which is optionally in conjugation with the two other substituents, where the number of atoms in Z which link the group of the formula (1) and the aromatic radical is an even number, where one or more non-adjacent C atoms may be replaced by $-O-$, $-S-$ or $-NR^1-$ or one or more C atoms may be substituted by a radical $R^1$ or halogen;
wherein in compounds of the formula (1), a 9,9'-spirobifluorene derivative, a 6,6- and/or 12,12-di- or tetra-substituted indenofluorene derivative, a tetraarylmethane derivative or a triptycene derivative is present in at least one of the radicals R,
wherein the structure of the formula (1) is pyridazine, pyrazine, or 1,3,5-triazine, with the proviso that R does not contain substituted or unsubstituted phenylpyridine, is incorporated between the emission layer and the cathode.

2. Organic electroluminescent device according to claim 1, characterised in that a hole-injection layer and/or a hole-transport layer and/or an electron-injection layer and/or an electron-transport layer is present.

3. Organic electroluminescent device according to claim 1, characterised in that the hole-blocking layer comprises at least 50% of compounds of the formula (1).

4. Organic electroluminescent device according to claim 3, characterised in that the hole-blocking layer consists only of compounds of the formula (1).

5. Organic electroluminescent device according to claim 1, characterised in that the hole-blocking material comprises more than one unit of the formula (1).

6. Organic electroluminescent device according to claim 1, characterised in that the molecules of the hole-blocking material have a non-planar structure.

7. Organic electroluminescent device according to claim 6, characterised in that at least one substituent R in the hole-blocking material contains at least one $sp^3$-hybridised carbon atom.

8. Organic electroluminescent device according to claim 7, characterised in that the $sp^3$-hybridised carbon atom is a quaternary carbon atom.

9. Organic electroluminescent device according to claim 1, characterised in that in compounds of the formula (1), a 9,9'-spirobifluorene derivative is present in at least one of the radicals R.

10. Organic electroluminescent device according to claim 1, characterised in that the glass transition temperature of the compounds of the formula (1) is >100° C.

11. Organic electroluminescent device according to claim 1, characterised in that the layer thickness of the hole-blocking layer is 1 to 50 nm.

12. Organic electroluminescent device according to claim 1, characterised in that the matrix for the phosphorescent emitter is selected from the classes of carbazoles, ketones, imines, phosphine oxides, phosphine sulfides, phosphine selenides, phosphazenes, sulfones, sulfoxides, silanes, polypodal metal complexes or oligophenylenes based on spirobifluorenes.

13. Organic electroluminescent device according to claim 1, characterised in that the phosphorescent emitter is a compound which contains at least one element having an atomic number of greater than 36 and less than 84.

14. Organic electroluminescent device according to claim 13, characterised in that the phosphorescent emitter contains at least one element selected from the elements consisting of molybdenum, tungsten, rhenium, ruthenium, osmium, rhodium, iridium, palladium, platinum, silver, gold and europium.

15. Organic electroluminescent device according to claim 1, characterised in that one or more layers are coated by a sublimation process.

16. Organic electroluminescent device according to claim 1, characterised in that one or more layers are coated by the OVPD (organic vapour phase deposition) process or with the aid of carrier-gas sublimation.

17. Organic electroluminescent device according to claim 1, characterised in that one or more layers are coated by a printing process.

18. An electronic device which comprises the organic electroluminescent device as claimed in claim 1, wherein the electronic device is an organic transistor, organic integrated circuit, organic solar cell, organic laser diode or photoreceptor.

19. A compound of the formula (2) comprising at least one 9,9'-spirobifluorene unit, characterised in that at least one 1,3,5-triazine unit is bonded to the 9,9'-spirobifluorene Formula (2)

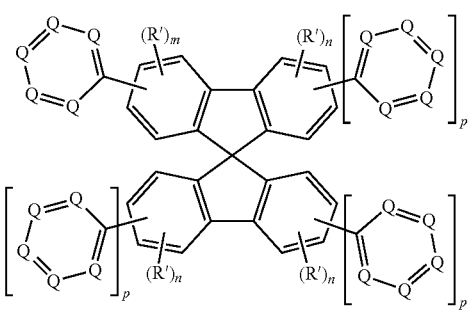

wherein
R is on each occurrence, identically or differently, H, $NO_2$, CN, $N(R^1)_2$, a straight-chain, branched or cyclic alkyl or alkoxy group having 1 to 40 C atoms, in which one or more non-adjacent $CH_2$ groups may be replaced by —$R^1C$=$CR^1$—, —C≡C—, $Si(R^1)_2$, $Ge(R^1)_2$, Sn$(R^1)_2$, —O—, —S— or —$NR^1$— and in which one or more H atoms may be replaced by F or an aromatic group $R^1$, or an aromatic or heteroaromatic ring system or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system, or an aromatic or heteroaromatic ring system bonded via a divalent group —Z— or an aryloxy or heteroaryloxy group, each having 1 to 40 aromatic C atoms, in which one or more H atoms may be replaced by F, Cl, Br or I or which may be substituted by one or more non-aromatic radicals R; a plurality of substituents R here may define a further mono- or polycyclic, aliphatic or aromatic ring system;

$R^1$ is on each occurrence, identically or differently, H or an aliphatic, aromatic or heteroaromatic hydrocarbon radical having 1 to 20 C atoms, in which a plurality of substituents $R^1$ or $R^1$ with R may also define a further mono- or polycyclic, aliphatic or aromatic ring system;

Q is on each occurrence, identically or differently, N or $CR^{10}$, with the proviso that three Q stand for nitrogen and two Q stand for $CR^{10}$;

$R^{10}$ is on each occurrence, identically or differently, H, $NO_2$, CN, a straight-chain, branched or cyclic alkyl or alkoxy group having 1 to 40 C atoms, in which one or more non-adjacent $CH_2$ groups may be replaced by —$R^1C$=$CR^1$—, —C≡C—, $Si(R^1)_7$, $Ge(R^1)_7$, Sn$(R^1)_2$, —O—, —S— or —$NR^1$— and in which one or more H atoms may be replaced by F or an aromatic group $R^1$, or an aromatic or heteroaromatic ring system or an aryloxy or heteroaryloxy group, each having 1 to 40 aromatic C atoms, in which one or more H atoms may be replaced by F, Cl, Br or I or which may be substituted by one or more non-aromatic radicals $R^{10}$; a plurality of substituents $R^{10}$ here may define a further mono- or polycyclic, aliphatic or aromatic ring system, or an aromatic or heteroaromatic ring system bonded via a divalent group —Z— or an aryloxy or heteroaryloxy group, each having 1 to 40 aromatic C atoms, in which one or more H atoms may be replaced by F, Cl, Br or I or which may be substituted by one or more non-aromatic radicals $R^{10}$; a plurality of substituents $R^{10}$ here may define a further mono- or polycyclic, aliphatic or aromatic ring system;

R' is on each occurrence, identically or differently, R or F, Cl, Br, I, $B(R^1)_2$ or $B(OR^1)_2$;

m is on each occurrence, identically or differently, 0, 1, 2 or 3;

n is on each occurrence, identically or differently, 0, 1, 2, 3 or 4, with the proviso that n must not be 4 if p=1;

p is on each occurrence, identically or differently, 0 or 1.

20. The compound according to claim 19, characterised in that the following applies to the symbols and indices:

R is on each occurrence, identically or differently, an aromatic or heteroaromatic ring system having 1 to 10 aromatic C atoms, which may be substituted by one or more non-aromatic radicals R, where a plurality of substituents R, both on the same ring and also on different rings, may together in turn define a further mono- or polycyclic, aliphatic or aromatic ring system;

R' is on each occurrence, identically or differently, R, a straight-chain, branched or cyclic alkyl group having 1 to 10 C atoms, in which one or more non-adjacent $CH_2$ groups may be replaced by —$R^1C$=$CR^1$—, —C≡C—, $Si(R^1)_2$, $Ge(R^1)_2$, Sn$(R^1)_2$, —O—, —S— or —$NR^1$—, or Br, I or $B(OR^1)_2$;

m is on each occurrence equal to 0;

n is on each occurrence, identically or differently, 0 or 1;

the further symbols and indices are as defined above under formulae (1) and (2).

21. The compound according to claim 19, characterised in that two triazine units are present, both bonded to the same fluorene sub-unit of the spirobifluorene.

22. Polymers or dendrimers comprising one or more compounds according to claim 19.

23. Electronic device comprising at least one compound, polymer or dendrimer according to claim 19.

24. Electronic device according to claim 23, characterised in that it is an organic light-emitting diode, an organic solar cell, an organic transistor, an organic integrated circuit, an organic laser diode or an organic photoreceptor.

25. Organic electroluminescent device according to claim 1, wherein

Z is on each occurrence, identically or differently, a straight-chain, branched or cyclic, conjugated radical having 1 to 40 C atoms, which is in conjugation with the two other substituents, where the number of atoms in Z which link the group of the formula (1) and the aromatic radical is an even number, where one or more non-adjacent C atoms may be replaced by —O—, —S— or —$NR^1$— or one or more C atoms may be substituted by a radical $R^1$ or halogen.

* * * * *